United States Patent [19]

Stauffer

[11] Patent Number: 4,878,756
[45] Date of Patent: Nov. 7, 1989

[54] METHOD AND APPARATUS FOR SENSING COLOR

[75] Inventor: Norman L. Stauffer, Arapahoe, Colo.

[73] Assignee: Honeywell Inc., Minneapolis, Minn.

[21] Appl. No.: 229,871

[22] Filed: Aug. 8, 1988

[51] Int. Cl.4 .......................................... G01N 21/25
[52] U.S. Cl. .................................... 356/406; 356/411
[58] Field of Search ............... 356/406, 407, 402, 411; 351/205

[56] References Cited

U.S. PATENT DOCUMENTS

| | | | |
|---|---|---|---|
| 4,551,022 | 11/1985 | Tagaya | 356/406 |
| 4,653,014 | 3/1987 | Mikam et al. | 356/406 |
| 4,768,873 | 9/1988 | Webb | 351/205 |

Primary Examiner—Leon Scott, Jr.
Attorney, Agent, or Firm—Charles L. Rubow

[57] ABSTRACT

A color detecting apparatus and process in which light from a source is directed to a surface whose color is to be measured through an aspheric lens situated so that reflected radiation is returned to the aspheric lens along a reversely directed path. The aspheric lens collimates the reflected light from the surface and directs it to two or more detectors which are tuned to receive energy in two or more preselected band widths along paths which are substantially of equal length with each detector receiving energy in substantially same cross-sectional area of the collimated beam.

34 Claims, 2 Drawing Sheets

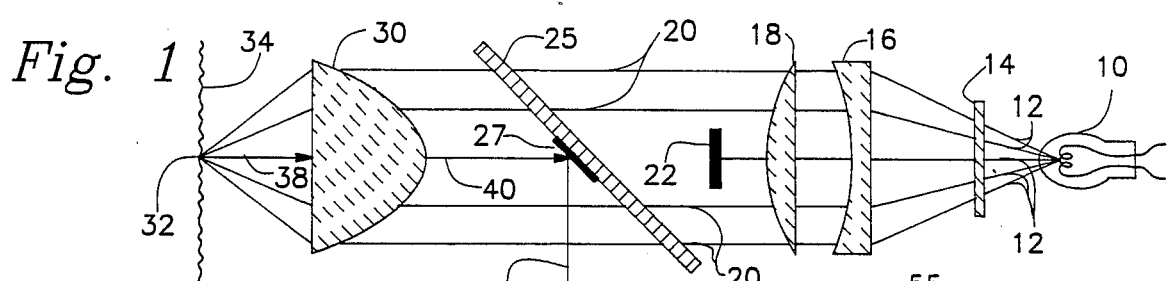
Fig. 1
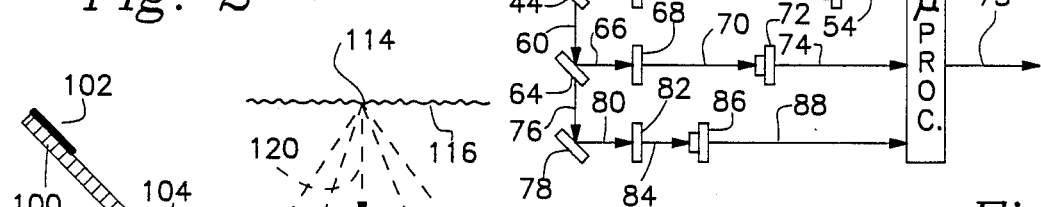
Fig. 2
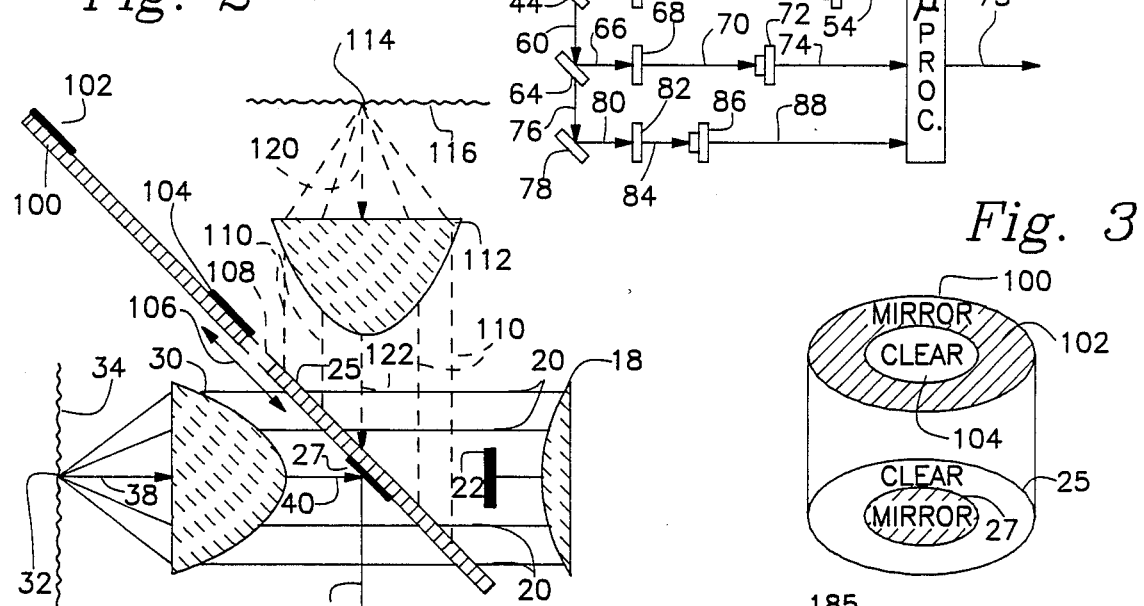
Fig. 3
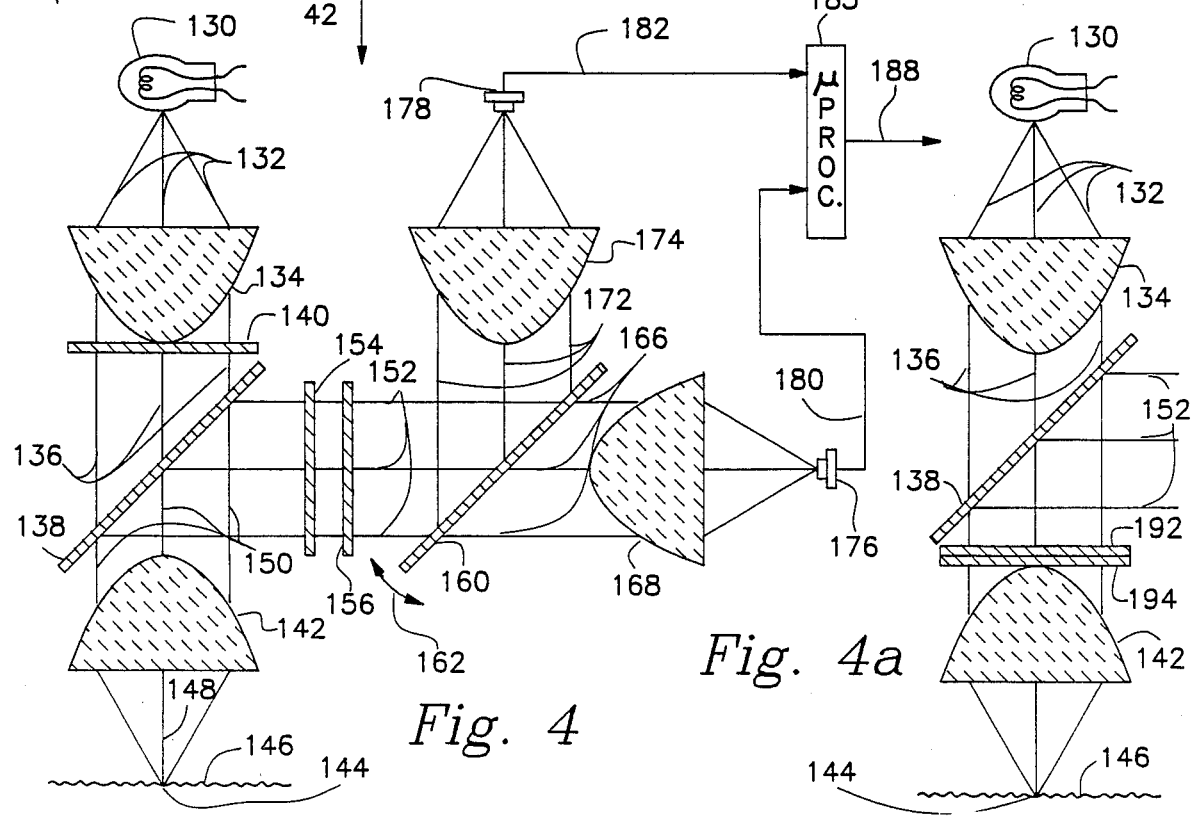
Fig. 4
Fig. 4a

METHOD AND APPARATUS FOR SENSING COLOR

BACKGROUND OF THE INVENTION

1. Field of the Invention.

The present invention pertains to the sensing of color and more particularly to an optical arrangement whereby the color of a surface is sensed utilizing light reflected from the surface and directed to at least two detectors characterized to respond to different wavelength bands. The output of the detectors is analyzed to determine the relative amounts of radiation in the bands as an indication of the color of the surface.

2. Description of the Prior Art.

Systems for sensing color have been devised in the past. One such system involves directing light through a spherical lens at an angle to the surface to be sensed and focussing the reflected light through filters that are arranged to pass only the primary colors, onto light responsive detectors to produce output signals intended to be indicative of the amount of each primary color present in the reflected energy.

Another such system, rather than using three separate filter-detector combinations, uses a single detector and a plurality of filters movable, one at a time, in the path of reflected light from the surface to the detector. The series of signals from the detector are analyzed to determine the color of the surface.

Several difficulties have been encountered with prior art systems such as described above. For example, these systems utilize spherical lenses to direct the beam of light onto the surface and focus it on the detectors. Spherical lenses have fairly large f numbers, typically greater than f1.4, and accordingly, the flux density of the light on the surface being investigated is limited. This is because the flux density depends on the area of the lens divided by the square of the distance to the surface and is inversely proportional to the square of the f member. Thus, the flux density decreases with the square of the f number making it undesirable to use lenses with large f numbers. For best results, it would be desirable to employ f numbers below 1 to obtain greater amounts of usable light but with spherical lenses this is not practically possible. Furthermore, when the light reflected from the surface is focussed onto the three detectors, as in the first system described above, each detector receives energy from a different area of the reflected beam, and each different area may have different amounts of the primary colors used to determine the color of the surface. Thus the reliability of such systems is poor. Furthermore, the filters and detectors when placed in the beam, in addition to receiving different amounts of primary colors are usually at different distances from the surface and accordingly receive different amounts of flux. Thus this system is, at best, a rather inaccurate representation of the amounts of primary colors in the surface being sensed and the resultant output is often in error. The alternate system described above is very slow in operation since the filters have to be moved into the reflected light path one at a time. Accordingly the alternate is unsatisfactory when color analysis is desired quickly as, for example, on a production line with products being moved rapidly past the color detector apparatus.

BRIEF DESCRIPTION OF THE INVENTION

The present invention overcomes the problems in the prior art by directing a collimated beam of energy through an aspheric lens whose f number is preferably less than 1, and by directing the beam substantially perpendicular to the surface being analyzed. The spot of energy striking the surface is therefore reflected back along the same general path to the aspheric lens which then operates to collimate the beam in the reverse direction. Means, such as a partly silvered mirror or other reflector takes a portion of the collimated reflected energy ad directs it to two or more filter detector combinations which are arranged to be spaced at equal distances from the surface. All of the detectors and filters used to sense specific wavelength bands of light receive the light from the same cross-sectional area and accordingly are subjected to the same amounts of the specific wavelengths involved. Furthermore, since the detectors are placed at the same distance from the surface, they are subjected to the same amount of flux and the errors which were present in the prior art systems are corrected. Also, because there is no need to move filters into the reflected light path, the system is very rapid and eminently useful for high speed operation such as in production lines.

BRIEF DESCRIPTION OF THE DRAWINGS

FIG. 1 shows a first embodiment of the present invention;

FIG. 2 shows the arrangement of FIG. 1 further including a reference surface for comparison;

FIG. 3 shows how the mirrors of FIG. 2 appear from the side;

FIG. 4 shows an alternate embodiment of the present invention and an arrangement for inhibiting specular reflections;

FIG. 4a shows an alternate arrangement for inhibiting specular reflections;

DETAILED DESCRIPTION OF THE PREFERRED EMBODIMENTS

Figure 5:
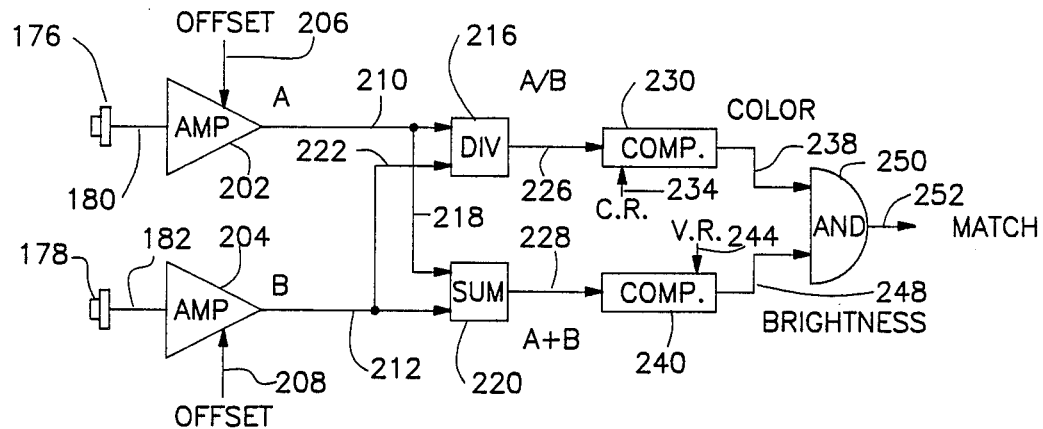
FIG. 5 shows a block diagram of an electronic circuit for analyzing the signals from the detectors of FIG. 4.

In FIG. 1, a source of radiation 10 which emits energy, containing at least several wavelengths in a selected spectrum. In the present invention, radiation in the visible spectrum will be used since it is most common, but it should be understood that non-visible light such as infrared radiation may be analyzed using the inventive concepts described herein. Light from source 10 is shown radiating along lines such as 12 to a filter 14 which may be desirable in order to correct the color temperature of the source 10, and then to a collimating lens system 16,18 so as to produce a beam of collimated energy along lines such as 20 in FIG. 1. A circular radiation blocking aperture 22 is shown in FIG. 1 positioned so as to block radiation in the central portion of the collimated beam 20 and, accordingly, the radiation passing from collimator 16,18 is in the form of a hollow cylinder of flux. It should be understood that the collimator 16,18 shown as two elements may be replaced by other types of collimators including an aspheric lens.

Beam 20 passes through a transparent member 25 having a mirrored surface 27 on the left side thereof and in the central blocked out portion of the beam 20. After passing through transparent member 25, beam 20 is focused by an aspheric lens 30 so as to form a spot of light 32 on a surface 34, the color of which is to be determined. In the preferred embodiment, the diameter of spot 32 is about 2.5 millimeters and the f number of lens 30 is less than 1.0 so that the flux density of the light reflected from surface 34 is as large as possible. While the light could be directed at an angle to surface 34, in the preferred embodiment, the optical axis of lens 30 is substantially perpendicular to surface 34 and thus, radiation reflected from spot 32 travels back to aspheric lens 30 along the same path as it arrived. A central portion of the reflected light is shown by arrow 38 traveling from surface 34 to aspheric lens 30 which operates to recollimate this reflected radiation so that it travels as a pencil of light along the path shown by arrow 40 so that it strikes mirror 27 on transparent member 25. Mirror 27 redirects the reflected energy downwardly along a path shown by arrow 42 to a first partly reflecting mirror 44 which in turn reflects a portion of the energy in the pencil of radiation 42 to the right along the path shown by arrow 46 to a first filter 48. Filter 48 may be arranged to pass a band of wavelengths in a first part of the spectrum to be analyzed. If, for example, it is desired to pass the primary colors, as was the case in the prior art, filter 48 could be arranged to pass a band of wavelengths around the blue part of the visible light spectrum.

This blue light travels along a path shown by arrow 50 to a first detector 52 which may be a silicon photodiode having a surface which is larger than the area of the pencil of light 50. Detector 50 then produces an electrical output shown by arrow 54 to a microprocessor 55.

The unused portions of the light in beam 42 are not discarded by partly reflecting mirror 44 as would be the case in the prior art but rather are passed through along a path shown by arrow 60 to a second partly reflecting mirror 64 which redirects a portion of the energy along a path shown by arrow 66 to a second filter 68. Filter 68 is arranged to pass a band of wavelengths different than that passed by. filter 48 and, if the primary colors are being used, could be arranged to pass a band of wavelengths around the red part of the visible spectrum along a path shown by arrow 70 to a second detector 72 which may also be a silicon photodiode with a surface larger than the area of beam 70. Detector 72 senses the amount of energy in the second wavelength band and produces an electrical signal shown by arrow 74 which is also presented to microprocessor 55. It should be noted that the cross-sectional area of the beam 50 intercepted by semi-transparent mirror 44 is the same as the cross-sectional area of the beam 70 intercepted by semi-transparent mirror 64. Accordingly, detectors 52 and 72 will receive the same cross-sectional area of energy thus avoiding one of the problems encountered in the prior art. It should also be noted that the distance from filter 48 to detector 52 is greater than the distance from filter 68 to detector 72. The difference in distance is chosen so as to compensate for the difference in path length encountered by the light being reflected off mirror 44 and light being reflected off mirror 64, i.e., the length of the path 60. Accordingly, detectors 52 and 72 are the same distance from the surface 34, thus overcoming another of the problems encountered by the prior art.

In some cases, merely looking at two frequency bands, i.e., that passed by filter 48 and that passed by filter 68 will be sufficient to determine the color of surface 34. Accordingly, in some circumstances, microprocessor 55 need only receive the signals from detectors 52 and 72 to produce an output shown by arrow 75 indicative of the color of the spot 32 on surface 34. The manner in which the color is determined from the outputs of detectors 52 and 62 will be explained in connection with FIGS. 5, 6, and 7, below.

When more than two wavebands of light are needed to determine the color of spot 32 on surface 34, it may be desirable to look at a third band of wavelengths in the light being reflected from spot 32. In such event, light passed by partly reflective mirror 64 is presented along a path shown by arrow 76 to a third partly reflecting mirror 78 which redirects the radiation along a path shown by arrow 80 to a third filter 82. Filter 82 will be arranged to pass a third band of wavelengths different than those passed by filters 48 and 68 and, if the primary colors are being used, may be arranged to pass a band of wavelengths around the color green in the visible spectrum along a path shown by arrow 84 to a third detector 86. Detector 86, like detectors 52 and 72 may be a silicone photodiode having a surface area larger than the area of beam 84. Detector 86 will produce an electrical output along a line shown as arrow 88 to the microprocessor 55 which will then compare the blue, red, and green components of the light being reflected from spot 32 to produce an output on arrow 75 indicative of the color of spot 32.

In some rare cases, where more than three bands of wavelengths are needed, a fourth etc. set of partly reflecting mirrors, filters and detectors, not shown, may be added on to the apparatus of FIG. 1 in similar fashion.

It may be desirable to have a reference surface of known color used for comparison with the light being reflected from surface 34 so as to be able to calibrate the equipment and obtain a more accurate indication of exact color. FIG. 2 shows an arrangement in which the system of FIG. 1 can incorporate a reference surface for this purpose. In FIG. 2 the elements to the right of lens 18 and below transparent member 25 in FIG. 1 have been omitted for simplicity. Furthermore, all of the elements of FIG. 2 that retain the same functions as elements of FIG. 1 have the same reference numerals and will not be further described herein.

In FIG. 2 transparent member 25 is again shown having a central mirror 27 in the blocked out portion of beam 20 and operable to direct the beam 40, reflected from surface 34, down along beam 42. FIG. 2 also shows an additional transparent member 100 having a peripheral mirror 102 on its right hand surface with an aperture 104 therein corresponding in size and shape to mirror 27. In the usual case, mirrors 27 and 102 and aperture 104 are circular and may be more clearly seen in FIG. 3. Transparent member 100 is moveable in a direction shown by arrow 106 in FIG. 2 and is connected to transparent member 25 as shown by dash lines 108. Accordingly, when desired, transparent member 100 may be moved downwardly and to the right, thus moving transparent member 25 out of the way (also downwardly and to the right) so that transparent member 100 replaces transparent member 25 in the beam 20. When this occurs, the hollow cylindrical beam 20 will be reflected by mirror 102 upwardly in FIG. 1 in a hollow cylindrical beam such as shown by dash lines 110 to a second aspherical lens 112 so as to be focused at a spot 114 on a reference surface 116. Reference surface 114 will be of a known color and accordingly energy which is reflected from spot 114 along a central path shown as dashed arrow 120 will pass back through aspherical lens 112 and be recollimated so as to travel downwardly in a pencil beam shown as dashed arrow 122. Since transparent member 100 will have replaced transparent member 25 in FIG. 2, the energy travelling along beam 122 will pass through the center aperture 104 of transparent member 100 and will then continue downwardly in a direction shown by arrow 42 to be analyzed by the semi-transparent mirrors, filters, and detectors described in connection with FIG. 1. Since surface 116 is of a known color, microprocessor 55 will receive components of known value from the outputs of the detectors to determine what the proper calibration is for the surface.

After calibration has occurred, transparent member 25 may then be moved upwardly and to the left to replace transparent member 100 and assume the position shown in FIG. 2 so that thereafter the radiation reflected from surface 34 may be analyzed and compared with the reference radiation to produce a meaningful output from microprocessor 55 in FIG. 1.

FIG. 3 shows a side view of the transparent members 25 and 100 as seen from the right in FIG. 2 and shows the relationship of mirror 27 to mirror 102 and aperture 104.

Referring now to FIG. 4, an alternate embodiment of the present invention is disclosed in which a source of radiation 130, which may be similar to the source 10 of FIG. 1, is shown producing radiation along paths such as shown by reference numeral 132 to an aspheric lens 134. It should be noted that the sources of radiation used in the description in the present invention appear as glowing filaments, other sources of radiation including lasers and simulated sunlight may also be utilized. Lens 134 operates to collimate the radiation from source 30 and pass a beam of radiation such as shown by lines 136 down to a partly reflecting mirror 138 placed at an angle such as 45° to the collimated beam 36. It is seen that collimation is accomplished here by an aspheric lens which is preferred to the collimator lenses 16, 18 of FIG. 1 because of simplicity and cost and greater flux density, but it should be understood that other collimators including the lens pair 16,18 of FIG. 1 could be used. Beam 36 from aspheric lens 134 is also shown passing through a polarizer 140 which may be used in some systems to minimize the amount of reflection of a specular nature as will be explained below. After passing through partly reflecting mirror 138, beam 136 is focused by a second aspheric lens 142 onto a spot 144 on a surface 146 whose color is to be determined. As was the case in FIG. 1, reflected energy from spot 144 moves back to aspheric lens 142 along paths such as shown by reference numeral 148 and is recollimated so as to pass upwardly in FIG. 4, in the opposite direction to beam 136, along a collimated beam shown by reference numeral 150. Partially reflective mirror 138 reflects beam 150 to the right in FIG. 4 in a collimated beam such as is shown by reference numeral 152 which is shown passing through a second polarizer 154, which like polarizer 140 may be desirable in some cases and will be described below, to a filter 156 which, like filter 14 in FIG. 1, may be used to correct the color temperature of the source. Beam 152 then engages a wavelength splitter element 160 shown at an angle of 45° to beam 152, but moveable to other angles in a direction shown by arrow 162 when desired. Wavelength splitter 160 may be a multi-layer color separation dichroic filter manufactured by the Corion Corporation of Holliston, Mass. and operates to pass wavelengths above a predetermined point and to reflect wavelengths below the predetermined point. For example, if the wavelengths of light emanated by source 130 and reflected from surface 146 contain wavelengths from say 400 nanometers to say 750 nanometers, then wavelength splitter 160 could be arranged so that it would pass wavelengths between 400 nanometers and say 600 nanometers and then reflect wavelengths from 600 nanometers to 750 nanometers. The exact pass and reflect capabilities of the wavelength splitter 160 can be adjusted by rotating the device in the direction shown by arrow 162. Accordingly, in FIG. 2, beam 152 will be split by wavelength splitter 160 so that wavelengths below the predetermined set point will pass in a collimated beam 166 to another aspheric lens 168 and those wavelengths above the predetermined point will pass in a collimated beam 172 to an aspheric lens 174. Aspheric lenses 168 and 174 focus there respective beams 166 and 172 onto detectors 176 and 178 respectively so that the outputs of these detectors on lines shown as arrows 180 and 182, respectively, represent the values of radiation received by the detectors 176 and 178 in the two chosen wavelength bands. In the example given above, the output or detector 176 will show one amount or radiation that lies between 400 and 600 nanometers while the output of detector 178 will show the amount of radiation received in the 600 to 750 nanometer wavelength. These signals are presented to a microprocessor 185 which will determine the relative amounts of radiation of the selected wavelengths in the manner to be described below and will produce an output on a line 188 indicative of the color of spot 144 on surface 146.

When surface 146 is relatively flat, a certain amount of specular reflection will occur which, because of its greater intensity than the diffuse radiation being analyzed, may produce difficulties in determining the proper color. In order to avoid or minimize the amount of specular reflection from surface 146, the polarizers 140 and 154 may be employed. In operation, polarizer 140 will polarize the beam 136 so that the light which travels to the surface 146 and reflected therefrom will continue to be polarized whereas the light that is reflected from surface 146 diffusely will become unpolarized. This reflected light in travelling back by beams 150 and 152 will pass through polarizer 154 whose plane of polarization will be such as to block the light that continues to be polarized but will pass the diffuse light. Accordingly, the polarized light which represents that portion of the reflection indicative of a specular surface will be eliminated or minimized and the detectors 176 and 178 will receive substantially only diffuse light for determining the color of surface 146.

FIG. 4a shows an alternate way of illuminating the specular reflections from surface 146. In FIG. 4a, the elements which are the same as in FIG. 4 have the same reference numerals and all of the elements to the right of partially reflecting mirror 138 have been eliminated for simplicity. In FIG. 4a the polarizer 140 has been eliminated and instead a polarizer 192 is shown in the beam 136 after it passes through the partially reflective mirror 138. Also shown in FIG. 4a is a quarter wave plate 194 placed just below polarizer 192 before the light is focused by aspheric lens 142 to a spot 144 on surface 146. By use of the polarizer 192 and the quarter wave plate 194, the specular reflections are eliminated because the light will be polarized in a first direction by polarizer 192 and then rotated 45°, for example by the quarter wave plate 194. The energy then striking surface 146, which is of a specular nature, will remain polarized and, as it passes through the quarter wave plate 194 in the opposite direction, will be rotated another 45° so that upon reaching polarizer 192, the light is now 90° and will thus be blocked by polarizer 192. A portion of the diffuse radiation, however, will pass through the quarter wave plate 194 and polarizer 192 and will produce the beam 152 for analyzation just as was the case in connection with FIG. 4.

Turning now to FIG. 5 which shows a first embodiment of a circuit for analyzing the signals produced by the detectors to determine their color or to determine whether they are within a predetermined amount of a desired color is shown. Detectors 176 and 178 which may be the same as those found in FIG. 4, are shown in FIG. 5 producing their outputs on lines 180 and 182 to a pair of operational amplifiers 202 and 204, respectively. Since it has been found that even when viewing a totally black surface, a certain amount of background signal is produced by detectors 176 and 178, operational amplifiers 202 and 204 are shown having offset inputs 206 and 208, respectively, which are used to cancel out the inherent background signal. Accordingly, the output of amplifier 202 seen on a line shown as arrow 210 will be indicative of the magnitude of radiation sensed by detector 176 in the preselected band width which, according to the example, is between 400 and 600 nanometers and is referred to in FIG. 5 as signal "A". Likewise, the output of operational amplifier 204 which is seen on a line shown as arrow 212 will be a signal of magnitude indicative of the radiation sensed by detector 178 in the other band width which, according to the example, is between 600 and 750 nanometers. This signal is identified as signal "B".

Signal A is presented from line 210 to a division circuit 216 and also by a line shown as arrow 218 to a sum circuit 220. Signal B is presented by arrow 212 to the sum circuit 220 and by a line shown arrow 222 to the division circuit 216. Accordingly, the output of division circuit 216, found on a line shown as arrow 226, will be indicative of the division of "A" by "B" and the output of the sum circuit 220 on a line shown as arrow 228 will be indicative of the addition of "A" and "B". Since the amount of signal from detector 176 compared to the amount of signal from detector 178 is related to the color of the signals being received by the detectors, the value A/B will be indicative of color. Likewise, since the addition of the signals seen by detectors 176 and 178 will be indicative of the brightness involved in the beam being received by the detectors, the value A+B will be indicative of the brightness of the surface.

The signal A/B on line 226 is presented to a comparator 230 which will operate to compare the value A/B with various predetermined values that may be stored in a memory to determine what the color represented by A/B truly is. For example, comparator 230 is shown having an additional input "C.R." on a line shown as arrow 234 which may be signals from a memory or which may be a predetermined value which is to be compared with A/B. In any event, comparator 230 will produce an output on a line shown as arrow 238 which will have a magnitude indicative of the color of the spot 144 on surface 146 or, in the case where the signal A/B is being compared with a predetermined reference signal will be a signal whether or not the color represented by A/B is within the range of desired colors as determined from the input 234.

In a similar fashion, the output A+B on line 228 is fed to comparator 240 which will compare the signal A+B with a predetermined brightness signals either in its internal memory or as received on a "V.R." input shown by arrow 244. Comparator 240 will therefore produce an output on a line shown by arrow 248 which is indicative of the brightness of the spot 144 on surface 146 or, when being compared with a predetermined reference brightness on line 244 will be indicative of whether or not the brightness is within predetermined limits supplied by the reference.

The outputs on lines 238 and 248 may then be presented to an AND circuit 250 which will produce an output on a line shown as arrow 252 when there are simultaneous signals on lines 238 and 248 at its inputs. An output on line 252 indicates that there is a proper match between the desired color and desired brightness of the spot being observed and thus will be indicative of a match between that desired brightness and color and the predetermined values of the reference brightness and color.

Figure 6:
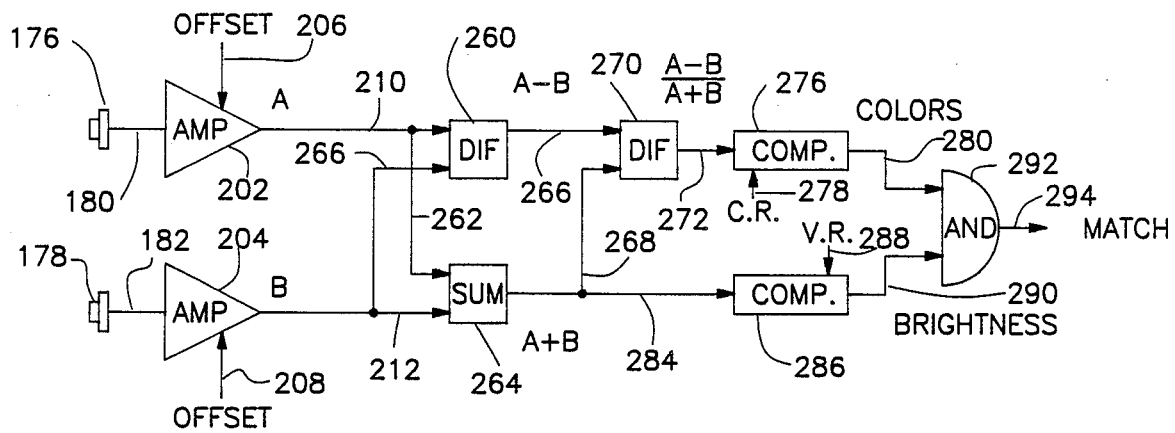
FIG. 6 shows a block diagram of an alternate electronic circuit for analyzing the signals of FIG. 4.

Because the value A/B is itself sensitive to variations in brightness, the ratio may not always truly be indicative of color. Accordingly, in FIG. 6, a circuit is devised which will remove the dependency of the color signal on absolute brightness by dividing the different between the two outputs of the detectors by the sum of the outputs of the two detectors. More particularly, in FIG. 6, the two detectors 176 and 178 are again shown producing outputs on lines shown as arrows 180 and 182, respectively, to a pair of operational amplifiers 202 and 204 having offset inputs 206 and 208 and operable to produce outputs "A" on line 210 and "B" on line 212 just as occurred in connection with FIG. 5. In FIG. 6, however, the "A" signal on line 210 is presented to a differencing circuit 260 and by a connection shown as arrow 262 to a sum circuit 264 while the "B" signal is presented on lines shown as arrow 212 to the sum circuit 264 and by a connection shown as arrow 266 to the differencing circuit 260. Differencing circuit 260 operates to subtract the signals "A" and "B" so as to produce an output A−B while the summing circuit operates to add the two signals to produce an output A+B as it did in connection with FIG. 5.

The A−B and A+B signals in FIG. 6 are presented over lines shown as arrows 266 and 268, respectively, to a division circuit 270 which operates to produce an output on a line shown as arrow 272 indicative of the division of the quantity A−B by the quantity A+B. As explained above, this signal, like the signal A/B, is indicative of color but does not have the dependence upon brightness that the A/B signal did.

As was the case in connection with FIG. 5, the color signal on line 272 is presented to a comparator 276 which has a color reference input 278 so that an output is produced on a line shown as arrow 280 indicative of the color of the spot 144 on surface 146 or indicative of a match between the color signal on line 272 and the color reference signal on line 278. Similarly, the sum signal is presented from circuit 264 on an output shown as line 284 to a comparator 286 which has a brightness reference "V.R." input on a line shown as arrow 288 so as to produce an output on a line shown as arrow 290 indicative of the brightness of the spot 144 on surface 146 of FIG. 4 or whether or not the brightness of the spot matches the brightness of the reference on line 288.

Likewise, as was the case in connection with FIG. 5, the inputs on lines 280 and 290 are presented to an AND gate 292 so that an output is produced on a line shown as arrow 294 to show a "match" whenever the brightness and the color both are within certain tolerance limits of the desired reference values on lines 278 and 288 respectively.

Figure 7:
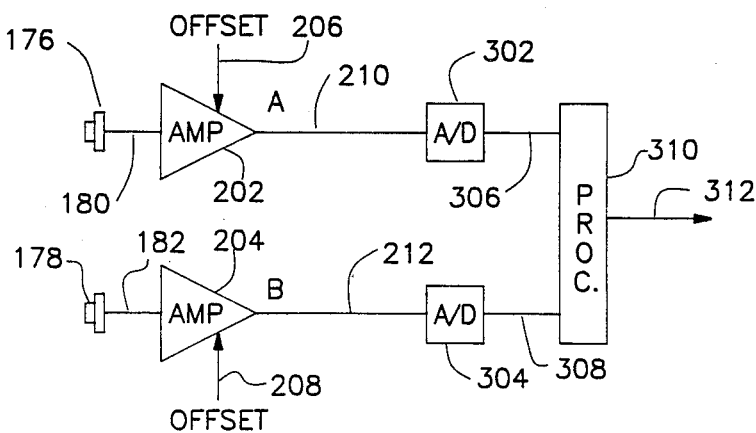
FIG. 7 shows a block diagram of another alternate circuit for analyzing the signals from the detectors of FIG. 4.

Of course, it should be understood that the entire process found in FIGS. 5 and 6 can be performed by a microprocessor having a memory storing the reference values or other color values to be compared with the inputs from the detectors and, accordingly in FIG. 7, the detectors 176 and 178 producing their outputs on lines 180 and 182, respectively, to operational amplifiers 202 and 204 each having an offset input shown on lines 206 and 208, respectively, are shown producing the A and B outputs on lines shown as arrows 210 and 212, respectively, to a pair of analog to digital converters 302 and 304 respectively. The digital outputs from converters 302 and 304 are produced on lines shown as arrows 306 and 308, respectively, and are presented to a microprocessor 310 which is shown producing the desired output on a line shown as arrow 312. Microprocessor 310 will have a memory therein containing the various colors that can be encountered by the detectors 176 and 178 and, accordingly, output on line 312 will be indicative of that color or, where it is desired to check the color against a predetermined reference, microprocessor 310 will have the reference values to be compared contained in a memory so that the output on line 312 will be indicative of a match between the actual signals from the spot 144 on surface 146 of FIG. 4 and the reference values.

It is therefore seen that I have provided a method and apparatus for determining the color of a surface in a more accurate way than was obtainable in the prior art. Many changes to the circuitry and structure shown in the preferred embodiments will occur to those skilled in the art, and accordingly I do not wish to be limited to the specific disclosures used in connection therewith. I intend only to be limited by the appended claims.

The embodiments of the invention in which an exclusive property or right is claimed are defined as follows:

1. Color sensing apparatus comprising:
    source means for producing radiation including at least first and second wavelength bands in a selected spectrum;
    collimating means receiving the radiation from the source and producing a collimated beam of radiation generally along a first axis;
    first substantially aspheric focusing means in said beam, focusing the radiation into a spot on a first surface, the color of which is to be sensed, said first focusing means receiving radiation reflected from the spot and re-collimating the reflected radiation back generally along the first axis;
    first radiation detecting means positioned a first optical distance from the surface to receive energy from a predetermined cross-sectional area of the beam of reflected radiation and responsive to radiation in substantially only the first wavelength band;
    second radiation detecting means positioned the first optical distance from the surface to receive energy from the predetermined cross-sectional area of the beam of reflected radiation and responsive to radiation in substantially only the second wavelength band; and
    analyzing means connected to the first and second radiation detection means and operable to determine the relative amounts of radiation in the first and second wavelength bands as an indication of the color of the surface at the spot.

2. Apparatus according to claim 1 wherein the first radiation detecting means includes a first radiation detector and a partly reflecting mirror operable to divert a first portion of the radiation to the first detector and to pass a second portion of the radiation to the second radiation detecting means.

3. Apparatus according to claim 2 wherein the second detecting means includes a second radiation detector and a mirror operable to divert the second portion of the radiation to the second detector.

4. Apparatus according to claim 3 further including third radiation detecting means positioned the first optical distance from the surface and responsive to radiation substantially only in a third wavelength band and wherein the mirror of the second detecting means is partly reflecting so as to pass a third portion of the radiation to the third detecting means.

5. Apparatus according to claim 4 wherein the first, second, and third wavelength bands each include substantially only one of the three primary colors, respectively.

6. Apparatus according to claim 1 further including first diverting means at a position along the first axis to divert a portion of the reflected radiation generally along a second axis and wherein the first and second detecting means are positioned to receive radiation diverted along the second axis.

7. Apparatus according to claim 6 wherein the first detecting means includes a first radiation detector and a partly reflecting mirror operable to further divert a first portion of the diverted radiation to the first detector and to pass a second portion of the radiation to the second detecting means.

8. Apparatus according to claim 6 further including second diverting means moveable to replace the first diverting means in the position along the first axis, the second diverting means diverting a portion of the radiation from the source generally along a third axis.

9. Apparatus according to claim 8 further including second substantially aspheric focusing means to receive radiation diverted along the third axis and focus the radiation into a spot on a second surface, the color of which is predetermined, said second focusing means receiving radiation reflected from the spot on the second surface and re-collimating the reflected radiation generally along the second axis to the first and second radiation detecting means.

10. Apparatus according to claim 9 wherein the first directing means includes a centrally positioned mirror, the exterior of which is transmissive to radiation and wherein the second directing means includes a mirror having a centrally located radiation transmitting portion.

11. Apparatus according to claim 6 further including partly reflecting means positioned along the second axis to divert a portion of the reflected radiation to the first detecting means and to pass a portion of the reflected radiation to the second detecting means.

12. Apparatus according to claim 11 wherein the first diverting means comprises a filter which operates to divert radiation in substantially only the first wavelength band and to pass radiation in substantially only the second wavelength band.

13. Apparatus according to claim 12 wherein the first diverting means comprises a color separation dichroic filter.

14. Apparatus according to claim 13 wherein the first diverting means is rotatable so as to adjust the wavelength bands diverted and passed.

15. Apparatus according to claim 11 wherein the first and second detecting means each include a substantially aspheric lens and a radiation detector.

16. Apparatus according to claim 6 wherein the first and second detecting means each include a substantially aspheric lens and a radiation detector.

17. Apparatus according to claim 1 wherein the first and second detecting means each produce an output indicative of the radiation received thereby and the analyzing means includes diverting means to receive the outputs and to produce a first resultant signal indicative of the ratio thereof.

18. Apparatus according to claim 17 further including first comparing means to receive the resultant output and to compare the first resultant signal with at least one reference value to produce a first comparison signal indicative of color.

19. Apparatus according to claim 17 wherein the analyzing means further includes sum means to receive the outputs and produce a second resultant signal indicative of the sum thereof.

20. Apparatus according to claim 19 further including second comparing means to receive the second resultant signal and to compare the second resultant signal with at least one reference value to produce a second comparison output indicative of brightness.

21. Apparatus according to claim 20 further including "and" means connected to the first and second comprising means to produce a match output upon receipt of simultaneous first and second comparison outputs.

22. Apparatus according to claim 1 wherein the first and second detecting means each produce an output indicative of the radiation received thereby, and wherein the analyzing means includes (a) difference means to receive the output and to produce a first resultant signal indicative of the difference thereof, (b) includes sum means to receive the outputs and to produce a second resultant signal indicative of the sum thereof, and (c) includes dividing means to receive the first and second resultant signals and to produce a combined output indicative of the ratio thereof.

23. Apparatus according to claim 22 further including first comparing means to receive the combined output and to compare the combined output with at least one reference value to produce a first comparison output indicative of color.

24. Apparatus according to claim 23 further including second comparing means to receive the second resultant signal and to compare the second resultant signal with at least one reference value to produce a second comparison output indicative of brightness.

25. Apparatus according to claim 24 further including "and" means connected to the first and second comparing means to produce a match output upon receipt of simultaneous first and second comparison outputs.

26. Apparatus according to claim 1 wherein the first and second detecting means each produce an output indicative of the radiation received thereby and the analyzing means includes a microprocessor connected to receive the first and second outputs and to compare them with predetermined color values prestored in memory, the microprocessor operable to produce a final output indicative of the color of the surface at the spot.

27. Apparatus according to claim 1 further including specular inhibit means mounted in the path of radiation from the source to the first and second detecting means to substantially eliminate radiation resulting from specular reflection.

28. Apparatus according to claim 27 wherein the specular inhibit means includes a first polarizer mounted between the source and the surface to polarize the radiation from the source and further includes a second polarizer mounted in the path of radiation reflected from the surface to block polarized radiation.

29. Apparatus according to claim 27 wherein the specular inhibit means includes a quarter wave plate mounted in the path of radiation from the source to the surface to rotate the radiation and further includes a polarizer mounted in the path of radiation reflected from the surface to block rotated radiation.

30. Apparatus according to claim 29 wherein the quarter wave plate operates to rotate the radiation by 45° and to further rotate the reflected radiation by 45° so that specular reflection is rotated 90° and is blocked by the polarizer.

31. The method of determining the color of an object comprising the steps of:
   (A) focusing a beam of radiation substantially collimated along a first axis and containing at least first and second wavelength bands, into a spot on the surface;
   (B) receiving radiation reflected from the spot through a substantially aspheric lens to produce a substantially collimated beam of reflected radiation substantially along the first axis;
   (C) separating radiation in the first wavelength band from radiation in the second wavelength band from a predetermined cross-sectional area of the reflected radiation;
   (D) directing the separated radiation in the first wavelength band to a first radiation detector positioned a first optical distance from the object;
   (E) directing the radiation in the second wavelength band to a second radiation detector positioned the first optical distance from the object; and
   (F) analyzing the outputs of the detectors to determine the relative amounts of radiation in the first and second wavelength bands as an indication of color.

32. The method of claim 31 wherein the step of analyzing the outputs includes:
   (F1) determining the ratio of the outputs; and
   (F2) comparing the ratio with a predetermined value.

33. The method of claim 31 wherein the step of analyzing the output includes:
   (F1) determining the sum and the difference of the outputs;
   (F2) determining the ratio of the sum and difference; and
   (F3) comparing the ratio with a predetermined value.

34. The method of claim 31 wherein the step of analyzing the output includes:
   (F1) digitizing the outputs; and
   (F2) comparing the digitized outputs to a stored value.

* * * * *